(12) United States Patent
Nobis

(10) Patent No.: US 7,915,457 B2
(45) Date of Patent: Mar. 29, 2011

(54) INTRAMOLECULAR PRINS REACTION AND CATALYSTS SUITABLE THEREFOR

(75) Inventor: Markus Nobis, Lyss (CH)

(73) Assignee: Symrise GmbH & Co. KG, Holzminden (DE)

( * ) Notice: Subject to any disclaimer, the term of this patent is extended or adjusted under 35 U.S.C. 154(b) by 207 days.

(21) Appl. No.: 11/992,639

(22) PCT Filed: Aug. 17, 2006

(86) PCT No.: PCT/EP2006/065387
§ 371 (c)(1),
(2), (4) Date: Dec. 3, 2008

(87) PCT Pub. No.: WO2007/039342
PCT Pub. Date: Apr. 12, 2007

(65) Prior Publication Data
US 2009/0093649 A1    Apr. 9, 2009

Related U.S. Application Data

(60) Provisional application No. 60/720,604, filed on Sep. 26, 2005.

(51) Int. Cl.
*C07C 35/08* (2006.01)
*C07F 7/02* (2006.01)

(52) U.S. Cl. ........................ 568/828; 556/173

(58) Field of Classification Search .................. 556/173; 568/828
See application file for complete search history.

(56) References Cited

U.S. PATENT DOCUMENTS 4,925,822 A * 5/1990 Slaugh et al. ................. 502/112
5,731,451 A * 3/1998 Smith et al. .................. 556/173
6,011,127 A * 1/2000 Monoi et al. ................. 526/127

FOREIGN PATENT DOCUMENTS

| EP | 0 271 716 A2 * | 6/1988 |
| EP | 1053974 A2 | 1/2002 |
| EP | 1225163 A2 | 7/2002 |
| JP | 2004/174429 | 6/2004 |

* cited by examiner

*Primary Examiner* — Porfirio Nazario Gonzalez
(74) *Attorney, Agent, or Firm* — Connolly Bove Lodge & Hutz LLP

(57) ABSTRACT

The present invention relates to a process for the preparation of a compound of the formula B having the following steps: provision of a compound of the formula A intramolecular reaction of the compound of the formula A in the presence of an aluminium siloxide of the formula (Ia) or (Ib).

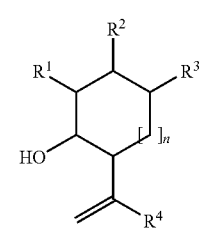

(B)

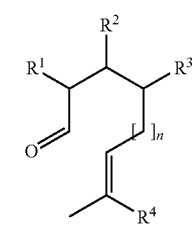

(A)

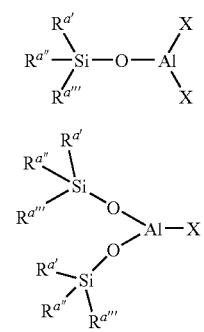

(Ia)

(Ib)

16 Claims, No Drawings

INTRAMOLECULAR PRINS REACTION AND CATALYSTS SUITABLE THEREFOR

RELATED APPLICATIONS

This application is a national stage application (under 35 U.S.C. 371) of PCT/EP2006/065387 filed Aug. 17, 2006, which claims benefit of U.S. Provisional application 60/720,604 filed Sep. 26, 2005.

The present invention primarily relates to a process for the preparation of a compound of the formula B from a compound of the formula A by an intramolecular Prins reaction (also known as intramolecular carbonyl-ene or oxygen-ene reaction) and to catalysts for this reaction (in particular based on aluminium- and silicon-containing compounds). The present invention also relates the corresponding use of suitable substances as a catalyst, in particular for catalysis of intramolecular Prins reactions. The invention furthermore relates to particular catalytically active reaction mixtures and reaction products.

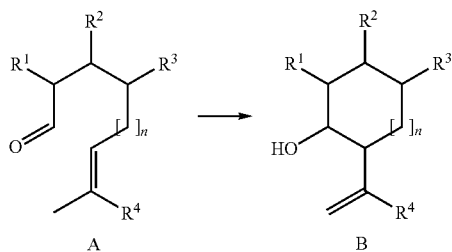

A known example of an intramolecular Prins reaction is the cyclization of citronella (3,7-dimethyl-6-octenal, A2) to isopulegol and its stereoisomers (8-p-menthen-3-ol; B2, i.e. isopulegol, neoisopulegol, isoisopulegol and neoisoisopulegol).

Isopulegol is of great interest for use as an odoriferous and aroma substance and can furthermore be converted into menthol by hydrogenation, as is shown in the following equation starting from d-citronellal (A2e) to give l-menthol (Ze) via l-isopulegol (B2iso).

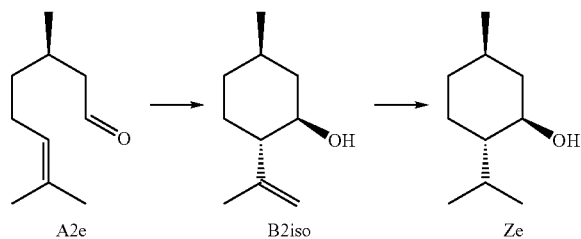

Depending on the stereochemical composition of the starting material A and the selectivity of the cyclization reaction, the product B formed can comprise a large number of stereoisomers (diastereomers and, where appropriate, enantiomers). A reaction procedure which is as selective as possible to give a particular diastereomer is usually aimed for.

The cyclization of d-citronellal to l-isopulegol in the presence of various Lewis acids is described in Synthesis 1978, 147, the best results (70% yield) having been achieved with equimolar amounts of zinc bromide in benzene. In this reaction, intermolecular addition products, inter alia, are observed as undesirable by-products, for example from the aldol condensation or the intermolecular Prins reaction. The l-isopulegol sought is formed with a selectivity of 94%, and a content of 6% is thus due to the further isopulegol isomers, d-neoisopulegol predominating among these isomers and the other isomers being formed only in traces.

In addition, the cyclization of citronella to give isopulegol has been attempted in the presence of numerous other (Lewis acid) catalysts, and in this respect reference may be made to the summary in EP 1 225 163 A2.

The possibility of separating off and re-using a Lewis acid from an aqueous medium after cyclization of citronellal to isopulegol has taken place is described in EP 1 053 974 A1. Using 34-40 mol % of (recyclized) zinc bromide as the catalyst, GC yields of isopulegol in the range of from about 82 to 89 GC % were obtained, the citronellal employed already containing more than 4% of isopulegol. In addition to the disadvantages of zinc bromide per se (heavy metal, poor handling), a difficult and energy-consuming separating off of the catalyst from the aqueous phase must be carried out in this process.

J. Am. Chem. Soc. 1980, 102, 7951-7953 describes the cyclization of citronellal to isopulegol in the presence of a molar equivalent of $Me_2AlCl$, isopulegol and neoisopulegol chiefly being obtained.

EP 1 225 163 A2 describes the conversion of citronellal into isopulegol using tris(2,6-diarylphenoxy)aluminium catalysts. Isopulegol is obtained in yields of up to more than 95% and with a selectivity of more than 99% starting from citronellal. Nevertheless, the catalysts employed are quite unstable and cannot be re-used or recycled when the reaction has ended. They are sensitive towards higher temperatures and aqueous media, and their preparation and handling present problems. A re-use of the tris(2,6-diarylphenoxy) aluminium catalysts disclosed is accordingly not described.

From the technical aspect, the catalyst systems to date are disadvantageous because of their sensitivity to exposure to heat and/or aqueous media. Re-usability or recycling is either not possible at all, or possible only with a high outlay.

There therefore continues to be a need for processes and catalyst systems which render possible the preparation of cyclization products in a good yield by means of an intramolecular Prins reaction, and allows simple isolation of the cyclization products, preferably by means of the separation processes which are usual in industry, such as, for example, distillation. The catalyst system should preferably be re-usable or recyclable and have substantially constant properties in respect of activity and selectivity (in formation of the cyclization products) over several reaction cycles.

The present invention is based on the object of providing such an improved process or catalyst system. In particular, the process and catalyst system should render possible a faster chemo- and diastereoselective cyclization of citronellal to isopulegol with the preferential formation of l-isopulegol compared with the catalyst systems known to date.

The object described in respect of the "process" aspect is achieved according to a first alternative by a process for the preparation of a compound of the formula B

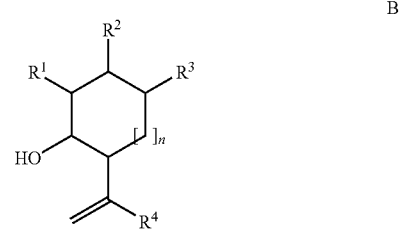

having the following steps:
  provision of a compound of the formula A

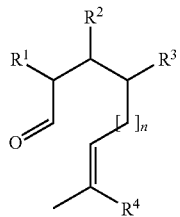

intramolecular reaction of the compound of the formula A in the presence of an aluminium siloxide of the formula (Ia) or (Ib)

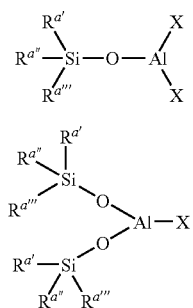

wherein in the formulae A and B the meaning of $R^1$, $R^2$, $R^3$, $R^4$ and n is identical and:
$R^1$, $R^2$, $R^3$ in each case independently of one another denote hydrogen or methyl,
$R^4$ denotes hydrogen or an alkyl radical having 1 to 6 C atoms,
n denotes 0, 1 or 2
and wherein in the formula (Ia) and (Ib):
$R^{a'}$, $R^{a''}$, $R^{a'''}$ in the substituent or the two substituents —$SiR^{a'}R^{a''}R^{a'''}$ of the aluminium siloxide of the formula (Ia) or (Ib) independently of one another and independently of the meaning in a second substituent —$SiR^{a'}R^{a''}R^{a'''}$ optionally present denote hydrogen or an organic radical, preferably a substituted or unsubstituted radical chosen from the group consisting of alkyl, heteroalkyl, cycloalkyl, cycloalkylalkyl, alkenyl, cycloalkenyl, cycloalkenylalkyl, alkynyl, cycloalkylalkynyl, alkoxy, cycloalkoxy, cycloalkylalkoxy, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, with the proviso that at least one of the radicals $R^{a'}$, $R^{a''}$, $R^{a'''}$ of each substituent —$SiR^{a'}R^{a''}R^{a'''}$ is not hydrogen,
wherein independently of one another also two or three of the radicals $R^{a'}$, $R^{a''}$, $R^{a'''}$ of each substituent —$SiR^{a'}R^{a''}R^{a'''}$ can be covalently bonded to one another, and
X in each case and independently of the meaning of a second X optionally present denotes an organic or inorganic substituent, but not hydrogen or a siloxy group having a substituent —$SiR^{a'}R^{a''}R^{a'''}$ as defined above.

The present invention is closely related to one of our own inventions which as been filed at the US Patent Office as U.S. provisional application 60/720,604. The content of the said US provisional application and of the associated patent family members is a constituent of the present application by way of reference.

Preferably, in the aluminium siloxides of the formulae (Ia) or (Ib) which are employed in a process according to the invention, X in each case independently of the meaning of a second X optionally present denotes an organic or inorganic substituent which is chosen from the group consisting of: branched or unbranched or cyclic alkyl, alkenyl or alkynyl having 1 to 30 C atoms; alkoxy having 1 to 30 C atoms; cycloalkoxy having a ring size of $C_3$-$C_{16}$; aryloxy; bisaryloxy; boric acid substituted by one or two organic radicals; chloride. Particularly preferably, X independently of the meaning of a second X optionally present denotes methyl, ethyl, n-propyl, iso-propyl, n-butyl, sec-butyl, iso-butyl, tert-butyl, alkoxy having 1 to 10 C atoms, cycloalkoxy having a ring size of $C_3$-$C_8$ or chloride. If X is a substituent which is a boric acid substituted by one or two organic radicals, the organic radicals are preferably aryl groups.

For preferred meanings of the substituents $R^{a'}$, $R^{a''}$, $R^{a'''}$, see below.

If the radicals $R^{a'}$, $R^{a''}$, $R^{a'''}$ are substituted, the following substituents are preferred:
hydroxyl,
$C_1$-$C_8$-alkyl, preferably methyl, ethyl, n-propyl, iso-propyl, n-butyl, iso-butyl, tert-butyl,
$C_3$-$C_{18}$-cycloalkyl, preferably cyclopropyl, cyclopentyl, cyclohexyl, cyclooctyl, cyclododecyl, cyclopentadecyl, cyclohexadecyl,
$C_2$-$C_8$-alkynyl, preferably ethynyl, propynyl,
$C_1$-$C_8$-perfluoroalkyl, preferably trifluoromethyl, nonafluorobutyl,
$C_1$-$C_8$-alkoxy, preferably methoxy, ethoxy, iso-propoxy, n-butoxy, iso-butoxy, tert-butoxy,
$C_3$-$C_{12}$-cycloalkoxy, preferably $C_3$-cycloalkoxy, $C_5$-cycloalkoxy, $C_6$-cycloalkoxy, $C_8$-cycloalkoxy, $C_{12}$-cycloalkoxy, $C_{15}$-cycloalkoxy, $C_{16}$-cycloalkoxy,
$C_1$-$C_{20}$-alkoxyalkyl, in which 1 to 5 $CH_2$ groups are replaced by oxygen, preferably —[—O—$CH_2$—$CH_2$—]$_v$-Q or —[—O—$CH_2$—CHMe-]$_v$-Q, wherein Q is OH or $CH_3$ and wherein v denotes an integer from 1 to 4,
$C_1$-$C_4$-acyl, preferably acetyl,
$C_1$-$C_4$-carboxyl, preferably $CO_2Me$, $CO_2Et$, $CO_2$ iso-Pr, $CO_2$tert-Bu,
$C_1$-$C_4$-acyloxy, preferably acetyloxy,
halide, preferably F or Cl,
$Si_1$-$Si_{10}$-silyl, and
$Si_1$-$Si_{30}$-siloxy or polysiloxy.

If one or more of the radicals $R^{a'}$, $R^{a''}$, $R^{a'''}$ independently of one another and independently of the meaning in a second substituent $SiR^{a'}R^{a''}R^{a'''}$ optionally present contains nitrogen, this nitrogen-containing radical is preferably stable to oxidation. In particular, under the oxidation conditions which prevail during the preparation of the silanol(s) (II) described below, the nitrogen containing radical should be inert, i.e. should not react with the oxidizing agent used there. Alternatively, stability to oxidation under the preparation conditions can be achieved by the introduction of N-protective groups, such as N-acylation, or by quaternization of the nitrogen atom.

According to a further aspect of the present invention, the object primarily described ("process" aspect) is alternatively achieved by a process for the preparation of a compound of the formula B

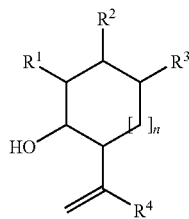

B having the following steps:
(a) provision of a compound of the formula A

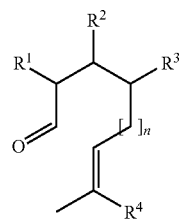

A (b) reaction
of an aluminium compound of the formula (IIIa) or (IIIb)

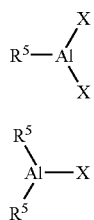 (IIIa)

 (IIIb)

wherein
each $R^5$ independently of the meaning of a second $R^5$ optionally present denotes an alkyl radical having 1 to 4 C atoms or an aryl radical or hydrogen and
X denotes an alkyl radical having 1 to 4 C atoms (methyl, ethyl, n-propyl, iso-propyl, n-butyl, sec-butyl, iso-butyl, tert-butyl) or chloride, with the proviso that X is bonded to Al more firmly than or as firmly as $R^5$
with one silanol or two or more different silanols of the formula (II),

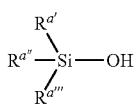 (II)

wherein:
$R^{a'}$, $R^{a''}$, $R^{a'''}$ in each silanol of the formula (II) employed independently of one another and independently of the meaning in a further silanol of the formula (II) optionally employed denote hydrogen or an organic radical, preferably an optionally substituted radical chosen from the group consisting of alkyl, heteroalkyl, cycloalkyl, cycloalkylalkyl, alkenyl, cycloalkenyl, cycloalkenylalkyl, alkynyl, cycloalkylalkynyl, alkoxy, cycloalkoxy, cycloalkylalkoxy, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, with the proviso that at least one of the radicals $R^{a'}$, $R^{a''}$, $R^{a'''}$ in each silanol employed is not hydrogen,
wherein independently of one another also two or three of the radicals $R^{a'}$, $R^{a''}$, $R^{a'''}$ in each of the silanols employed can be covalently bonded to one another,
wherein the molar ratio of aluminium compound of the formula (IIIa) or (IIIb) to the total amount of the one silanol or the two or more different silanols of the formula (II) is greater than 1:3,
(c) in situ and/or within 1 hour after the start of the reaction according to step (b), contacting of the compound of the formula A with the reaction product obtained in step (b) and intramolecular reaction of the compound of the formula A.

In this context, the "proviso that X is bonded to Al more firmly than $R^5$" means that on reaction of the aluminium compound of the formula (IIIa) or (IIIb) with the or the at least two different silanols of the formula (II), the radical(s) $R^5$ are preferentially substituted. Since the molar ratio of aluminium compounds of the formula (IIIa) or (IIIb) to the total amount of the one or the two different silanols of the formula (II) is greater than 1:3, if the proviso according to the invention is adhered to, no aluminium compounds trisubstituted by siloxy are obtained, but aluminium siloxides of the formula (Ia) or (Ib) are regularly obtained.

The process according to the invention (according to the first and second alternative) for the preparation of a compound of the formula B differ substantially in that according to the second alternative, the active catalyst (reaction product of the reaction of the aluminium compound of the formula (IIIa) or (IIIb) with the silanol of the formula (II)) is formed during the process according to the invention, while according to the first alternative aluminium siloxides (catalysts) of the formula (Ia) or (Ib) are already used as starting substances.

As mentioned, in the reaction (in the above step (b)) of the aluminium compound of the formulae (IIIa) or (IIIb) with the silanols of the formula (II) in the corresponding stoichiometry, the aluminium siloxides of the formulae (Ia) or (Ib) conventionally result. However, working up and optionally characterization, for example, of the reaction products of the reaction is not necessary according to the invention.

In the processes according to the invention according to the first or second alternative, for the compounds of the formulae A and B, preferably: $R^1$, $R^2$, $R^3$ in each case independently of one another denote hydrogen or methyl, $R^4$ denotes hydrogen or an alkyl radical having 1 to 6 C atoms, n denotes 0, 1 or 2.

Processes according to the invention (according to the first or the second alternative) which are particularly preferred are those wherein, in the formulae A and B: $R^1$ and $R^2$ in each case independently of one another denote hydrogen or methyl,
$R^3$ denotes hydrogen,
$R^4$ denotes methyl,
n denotes 0 or 1.

Processes according to the invention (according to the first or second alternative) which are very particularly preferred are those wherein the compound of the formula A is chosen from the group consisting of 2,6-dimethyl-5-heptenal and citronellal (3,7-dimethyl-6-octenal; A2).

The preferred compounds B1 and B2 (is opulegol) can be prepared from these compounds of the formula A

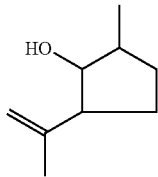
B1

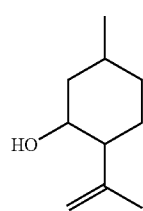
B2

The aluminium siloxides of the formula (Ia) and (Ib) can generally be prepared by a procedure such as corresponds to process step (b) according to the second alternative of a process according to the invention for the preparation of a compound of the formula B. The preparation of the aluminium siloxides of the formula (Ia) or (Ib) can otherwise be carried out analogously to the reaction of trialkylaluminium compounds with the corresponding silanols in accordance with Can. J. Chem. 1992, 70, 771-778. For preferred preparation processes, see below.

Starting from compounds of the formulae (Ia) or (Ib), employed as the educt, in which X e.g. denotes chlorine, methyl, ethyl, propyl, n-butyl, tert-butyl, however, product compounds of the formulae (Ia) or (Ib) in which X denotes ethyl, propyl can also be prepared. The exchange of the groups X takes place here e.g. by consecutive reaction by the mechanism of a hydroalumination with prior beta-hydrogen elimination by reaction of the educt compound of the formulae (Ia) or (Ib) with alkenes having a carbon number of between 5 and 20.

Alternatively, aluminium siloxides of the formulae (Ia) or (Ib), employed as the educt, where X=H, methyl, ethyl, propyl, n- and tertiary butyl, can be converted by addition of Brönstedt acid compounds into product aluminium siloxides of the formula (Ia) or (Ib) in which X=chlorine, acetate, formate, propionate, butyrate, isobutyrate.

Examples of the preparation (and trans-substitution) of aluminium siloxides of the formula (Ia) and (Ib) are given below.

Preferred process embodiments by way of example for achieving aluminium siloxides of the formulae (Ia) or (Ib) are shown in the following equations:

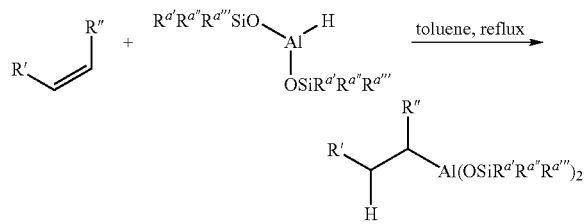

R′, R″ = alkyl, aryl, cycloalkyl

-continued

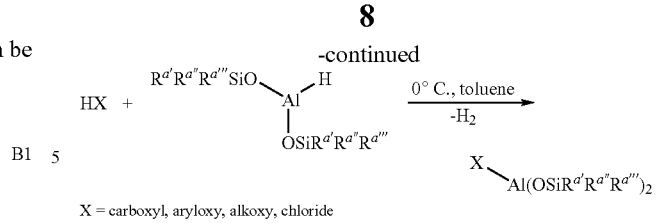

X = carboxyl, aryloxy, alkoxy, chloride

Preferably, in the process according to the invention, the aluminium siloxide of the formulae (Ia) or (Ib) or the reaction production of the reaction of the aluminium compound (IIIa) or (IIIb) with the silanols (II) is prepared in situ and/or is freshly prepared.

In the context of the present invention, it has been found, surprisingly, that the catalysts to be employed according to the invention, i.e. aluminium siloxides of the formulae (Ia) or (Ib) having the abovementioned meaning of the radicals $R^{a'}$, $R^{a''}$, $R^{a'''}$ and X or the said reaction products of a reaction of aluminium compounds of the formula (IIIa) or (IIIb) with silanols of the formula (II) render possible in an extremely selective manner the conversion of compounds of the formula A into the compounds of the formula B, but in particular the conversion of the compound A2 into the compound B2.

The catalysts to be employed are distinguished by an easy and flexible accessibility and an adequate stability.

The intramolecular Prins reaction using the catalysts to be employed according to the invention, in particular using the catalysts (aluminium siloxides) of the formulae (Ia) or (Ib), for the preparation of isopulegol (B2) from citronellal (A2) is distinguished in that isopulegol and neoisopulegol are chiefly obtained with a very high selectivity over a wide temperature range, and the diastereomers isoisopulegol and neoisoisopulegol are formed only in traces. For the selectivities to be achieved and the temperatures suitable for carrying out the reaction, see below.

In our own studies starting from citronellal (A2), it was found, compared with the tris(2,6-diarylphenoxy)aluminium catalysts according to EP 1 225 163 A2 which are described above, that the intramolecular Prins reaction proceeds significantly faster in the presence of the catalysts to be employed according to the invention, in particular of the formulae (Ia) or (Ib). The catalysts to be employed according to the invention, in particular of the formula (Ia) or (Ib), are significantly more stable towards exposure to heat and towards aqueous media than those described in EP 1 225 163 A2. Furthermore, when the tris(2,6-diarylphenoxy)aluminium catalysts according to EP 1 225 163 A2 were employed, in addition to the formation of the desired cyclization products (in particular B2), the intermolecular ester formation according to the Tischtschenko-Claisen reaction is also observed to a small extent.

Processes according to the invention which are particularly preferred are those in which the intramolecular reaction of the compound of the formula A is carried out in a diluent, the boiling point of which is higher than that of the compounds of the formulae A and B or after the intramolecular reaction of the compound of the formula A has taken place, a diluent, the boiling point of which is higher than that of the compounds of the formulae A and B, is added, having the following further step:
separating off, by distillation, of the compound of the formula B from the diluent and the aluminium siloxide of the formulae (Ia) or (Ib) or the reaction product of the reaction of the aluminium compound (IIIa) or (IIIb) with the silanol(s) (II).

The catalyst (aluminium siloxide of the formula (Ia) or (Ib) or mixture and/or reaction product of the reaction of the aluminium compound (IIIa) or (IIIb) with the silanol(s) (II)) employed in the process according to the invention is re-usable and recyclable. A particularly preferred process according to the invention accordingly comprises the following further step:

renewed use of the aluminium siloxide of the formulae (Ia) or (Ib) or of the reaction product of the reaction of the aluminium compound (IIIa) or (IIIb) with the silanol(s) (II) in the intramolecular reaction of the compound of the formula A In this context also, details are given below.
The present invention also relates to the use
either of an aluminium siloxide of the formula (Ia) or (Ib), wherein X has one of the abovementioned meanings,

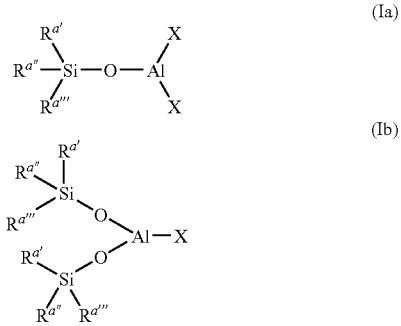

or of a reaction product of a reaction
of an aluminium compound of the formulae (IIIa) or (IIIb)

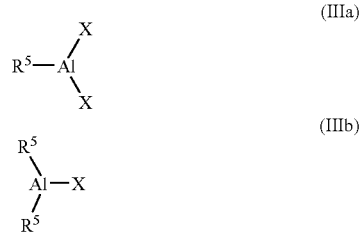

wherein
$R^5$ denotes an alkyl radical having 1 to 4 C atoms, an aryl radical or hydrogen and
X denotes an alkyl radical having 1 to 4 C atoms or chloride, with the proviso that
X is bonded to Al more firmly than or as firmly as $R^5$
with one silanol or two or more different silanols of the formula (II),

wherein the molar ratio of aluminium compound of the formulae (IIIa) or (IIIb) to the total amount of the one or the different silanols of the formula (II) is greater than 1:3, wherein:
$R^{a'}$, $R^{a''}$, $R^{a'''}$ in the substituent or the two substituents —$SiR^{a'}R^{a''}R^{a'''}$ of the aluminium siloxide of the formula (I) independently of one another and independently of the meaning in a second substituent —$SiR^{a'}R^{a''}R^{a'''}$ optionally present or in each silanol of the formula (II) employed independently of one another and independently of the meaning in a further silanol of the formula (II) optionally employed denote hydrogen or an organic radical, preferably a substituted or unsubstituted radical chosen from the group consisting of alkyl, heteroalkyl, cycloalkyl, cycloalkylalkyl, alkenyl, cycloalkenyl, cycloalkenylalkyl, alkynyl, cycloalkylalkynyl, alkoxy, cycloalkoxy, cycloalkylalkoxy, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, with the proviso that at least one of the radicals $R^{a'}$, $R^{a''}$, $R^{a'''}$ in each silanol employed is not hydrogen, wherein independently of one another also two or three of the radicals $R^{a'}$, $R^{a''}$, $R^{a'''}$ in each of the substituents —$SiR^{a'}R^{a''}R^{a'''}$ or each of the silanols employed can be covalently bonded to one another, as a catalyst, in particular for the catalysis of intramolecular Prins reactions.

In respect of preferred groups $R^{a'}$, $R^{a''}$, $R^{a'''}$ and substituents X, that stated above in respect of the processes according to the invention applies accordingly.

As likewise already emerges from the statements regarding the processes according to the invention, a preferred use is that for the preparation of a compound B

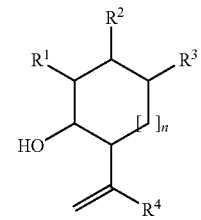

B from of a compound of the formula A

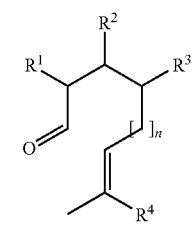

A wherein in the formulae A and B $R^1$, $R^2$, $R^3$, $R^4$ and n in each case have the same meaning and:
$R^1$, $R^2$, $R^3$ in each case independently of one another denote hydrogen or methyl,
$R^4$ denotes hydrogen or an alkyl radical having 1 to 6 C atoms,
n denotes 0, 1 or 2.

In respect of particularly preferred uses, that stated above in respect of particularly preferred processes according to the invention applies accordingly.

A further aspect of the present invention relates to novel catalysts and Lewis acids which are suitable in particular for use in the processes described above. The best results were achieved in the processes described above using these novel catalysts and Lewis acids.

Preferred catalysts and Lewis acids are novel aluminium siloxides of the formulae (Ia) or (Ib); in this context, see above.

The aluminium siloxides which are suitable for use in processes according to the invention and their use in the Prins reaction have not hitherto been described. The present invention thus also relates to aluminium siloxides of the formulae (Ia) or (Ib)

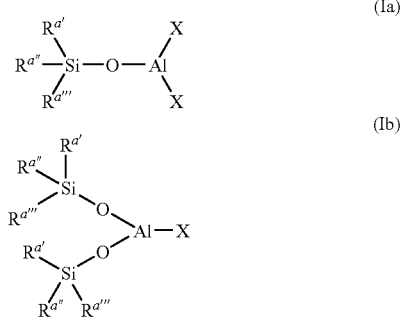

wherein in the formulae (Ia) and (Ib):
$R^{a'}$, $R^{a''}$, $R^{a'''}$ in the substituent or the two substituents —$SiR^{a'}R^{a''}R^{a'''}$ independently of one another and independently of the meaning in a second substituent —$SiR^{a'}R^{a''}R^{a'''}$ optionally present denote hydrogen or an organic radical, preferably a substituted or unsubstituted radical chosen from the group consisting of alkyl, heteroalkyl, cycloalkyl, cycloalkylalkyl, alkenyl, cycloalkenyl, cycloalkenylalkyl, alkynyl, cycloalkylalkynyl, alkoxy, cycloalkoxy, cycloalkylalkoxy, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, with the proviso that at least one of the radicals $R^{a'}$, $R^{a''}$, $R^{a'''}$ of each substituent —$SiR^{a'}R^{a''}R^{a'''}$ is not hydrogen,
wherein independently of one another also two or three of the radicals $R^{a'}$, $R^{a''}$, $R^{a'''}$ of each substituent —$SiR^{a'}R^{a''}R^{a'''}$ can be covalently bonded to one another, and wherein X independently of the meaning of a second X optionally present denotes an organic or inorganic substituent, but not hydrogen or a siloxy group having a substituent —$SiR^{a'}R^{a''}R^{a'''}$ defined above.

The compounds $Al(OSiPh_3)_3$ (THF) and $Al(OSiPh_3)_3$ $(H_2O)(THF)_2$ are indeed already known from Can. J. Chem. 1992, 70, 771-778. However, these compounds and all the further compounds (including intermediates) disclosed in the said document are not part of the present invention.

In the aluminium siloxides according to the invention, in each case X independently of the meaning of a second X optionally present preferably denotes an organic substituent which is chosen from the group consisting of: branched or unbranched alkyl, alkenyl or alkynyl having 1 to 30 C atoms; alkoxy having 1 to 30 C atoms; cycloalkoxy having a ring size of $C_3$-$C_{16}$; aryloxy; bisaryloxy; boric acid substituted by one or two organic radicals; chloride. In this context, compare the above comments on preferred processes according to the invention.

Preferably, in the aluminium siloxides according to the invention each X independently of the meaning of a second X optionally present preferably denotes an alkyl radical which is chosen from the group consisting of: n-propyl, iso-propyl, n-butyl, sec-butyl, iso-butyl, tert-butyl, alkyl having 5 to 30 C atoms.

Further preferred meanings of $R^{a'}$, $R^{a''}$, $R^{a'''}$ and X emerge from the statements on processes according to the invention.

In addition to the said aluminium siloxides according to the invention, the present invention also relates, however, to reaction mixtures or reaction products, which are suitable as a catalyst, of a reaction of an aluminium compound of the formula (IIIa) or (IIIb)

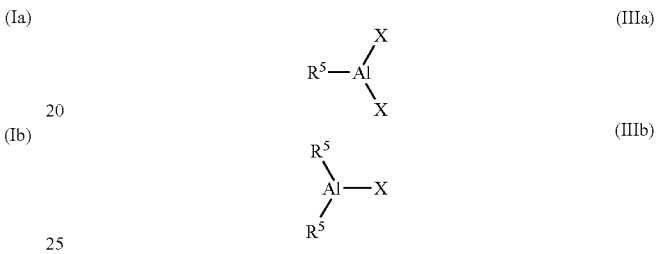

wherein
$R^5$ denotes an alkyl radical having 1 to 4 C atoms or an aryl radical and each X denotes independently of the meaning of a second X (optionally present) methyl, ethyl, n-propyl, iso-propyl, n-butyl, sec-butyl, iso-butyl, tert-butyl, an aryl radical or chlorine.
with the proviso that X is bonded to Al more firmly than or as firmly as $R^5$,
with one silanol or two or more different silanols of the formula (II),

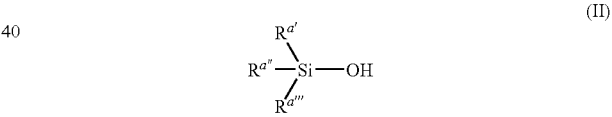

wherein:
$R^{a'}$, $R^{a''}$, $R^{a'''}$ in each silanol of the formula (II) employed independently of one another and independently of the meaning in a further silanol of the formula (II) optionally employed denote hydrogen or an organic radical, preferably an optionally substituted radical chosen from the group consisting of alkyl, heteroalkyl, cycloalkyl, cycloalkylalkyl, alkenyl, cycloalkenyl, cycloalkenylalkyl, alkynyl, cycloalkylalkynyl, alkoxy, cycloalkoxy, cycloalkylalkoxy, aryl, heteroaryl, arylalkyl, cycloalkylaryl, cycloalkenylaryl, cycloalkylheteroaryl, heterocycloalkylaryl, heterocycloalkenylaryl, heterocycloalkenylheteroaryl and heteroarylalkyl, with the proviso that at least one of the radicals $R^{a'}$, $R^{a''}$, $R^{a'''}$ in each silanol employed is not hydrogen,
wherein independently of one another also two or three of the radicals $R^{a'}$, $R^{a''}$, $R^{a'''}$ in each of the silanols employed can be covalently bonded to one another,
wherein the molar ratio of aluminium compound of the formula (IIIa) or (IIIb) to the total amount of the one silanol or the two or more different silanols of the formula (II) is greater than 1:3.

Particularly preferred processes according to the invention as well as, uses aluminium siloxides, reaction mixtures or reaction products according to the invention are those wherein $R^{a'}$, $R^{a''}$, $R^{a'''}$ in the substituent or the two substituents —$SiR^{a'}R^{a''}R'''$ of the aluminium siloxide of the formula (Ia) or (Ib) independently of one another and independently of the meaning in a second substituent —$SiR^{a'}R^{a''}R^{a'''}$ optionally present or in each silanol of the formula (II) employed independently of one another and independently of the meaning in a further silanol of the formula (II) optionally employed denote a substituted or unsubstituted radical which is chosen from the group consisting of: $C_1$-$C_{20}$-alkyl, $C_1$-$C_{20}$-heteroalkyl, $C_3$-$C_{20}$-cycloalkyl, $C_4$-$C_{20}$-cycloalkylalkyl, $C_2$-$C_{20}$-alkenyl, $C_3$-$C_{20}$-cycloalkenyl, $C_4$-$C_{20}$-cycloalkenylalkyl, $C_2$-$C_{20}$-alkynyl, $C_5$-$C_{20}$-cycloalkylalkynyl, $C_1$-$C_{20}$-alkoxy, $C_3$-$C_{20}$-cycloalkoxy, $C_5$-$C_{20}$-cycloalkylalkoxy, $C_3$-$C_{25}$-aryl, $C_2$-$C_{25}$-heteroaryl, $C_4$-$C_{25}$-arylalkyl, $C_8$-$C_{25}$-cycloalkylaryl, $C_8$-$C_{25}$-cycloalkenylaryl, $C_5$-$C_{25}$-Cycloalkylheteroaryl, $C_8$-$C_{25}$-heterocycloalkylaryl, $C_8$-$C_{25}$-heterocycloalkenylaryl, $C_8$-$C_{25}$-heterocycloalkenylheteroaryl and $C_3$-$C_{25}$-heteroarylalkyl, wherein independently of one another also two or three of the radicals $R^{a'}$, $R^{a''}$, $R^{a'''}$ can be covalently bonded to one another.

In this context, $R^{a'}$, $R^{a''}$, $R^{a'''}$ preferably independently of one another denote an optionally substituted radical chosen from the group consisting of $C_1$-$C_{10}$-alkyl, $C_3$-$C_{10}$-cycloalkyl, $C_4$-$C_{12}$-cycloalkylalkyl, $C_2$-$C_{10}$-alkenyl, $C_3$-$C_{12}$-Cycloalkenyl, $C_4$-$C_{12}$-cycloalkenylalkyl, $C_2$-$C_{10}$-alkynyl, $C_5$-$C_{12}$-cycloalkylalkynyl, $C_3$-$C_{20}$-aryl, $C_2$-$C_{20}$-heteroaryl, $C_4$-$C_{20}$-arylalkyl, $C_8$-$C_{20}$-cycloalkylaryl, $C_8$-$C_{20}$-cycloalkenylaryl, $C_5$-$C_{20}$-cycloalkylheteroaryl, $C_8$-$C_{20}$-heterocycloalkylaryl, $C_8$-$C_{20}$-heterocycloalkenylaryl, $C_8$-$C_{20}$-heterocycloalkenylheteroaryl and $C_4$-$C_{20}$-heteroarylalkyl.

Particularly preferably:

$R^{a'}$, $R^{a''}$, $R^{a'''}$ independently of one another denote an optionally substituted radical chosen from the group consisting of $C_1$-$C_{10}$-alkyl, $C_3$-$C_{10}$-cycloalkyl, $C_4$-$C_{12}$-cycloalkylalkyl, $C_6$-$C_{20}$-aryl, $C_2$-$C_{20}$-heteroaryl, $C_7$-$C_{20}$-arylalkyl, $C_8$-$C_{20}$-cycloalkylaryl, $C_8$-$C_{20}$-cycloalkenylaryl, $C_6$-$C_{20}$-cycloalkylheteroaryl, $C_8$-$C_{20}$-heterocycloalkylaryl, $C_8$-$C_{20}$-heterocycloalkenylaryl, $C_8$-$C_{20}$-heterocycloalkenylheteroaryl and $C_4$-$C_{20}$-heteroarylalkyl.

Very particularly preferably:

$R^{a'}$, $R^{a''}$, $R^{a'''}$ in the substituent or the two substituents —$SiR^{a'}R^{a''}R^{a'''}$ independently of one another and independently of the meaning in a second substituent —$SiR^{a'}R^{a''}R^{a'''}$ optionally present or in each silanol of the formula (II) employed independently of one another and independently of the meaning in a further silanol of the formula (II) optionally employed denote a substituted or unsubstituted radical chosen from the group consisting of $C_6$-$C_{20}$-aryl, $C_3$-$C_{20}$-heteroaryl, $C_8$-$C_{20}$-cycloalkylaryl, $C_8$-$C_{20}$-cycloalkenylaryl, $C_7$-$C_{20}$-cycloalkylheteroaryl, $C_8$-$C_{20}$-heterocycloalkylaryl, $C_8$-$C_{20}$-heterocycloalkenylaryl and $C_8$-$C_{20}$-heterocycloalkenylheteroaryl.

In processes and uses according to the invention and aluminium siloxides, reaction mixtures and reaction products according to the invention, for the aluminium siloxide of the formula (Ia) or (Ib) and the silanols of the formula (II), preferably:

all the radicals $R^{a'}$, $R^{a''}$, $R^{a'''}$ are identical.

The catalytic activity of reaction mixtures according to the invention (as defined above) is presumably based on the formation of aluminium siloxides of the formula (Ia) or (Ib) according to the invention; however, this is not clarified conclusively.

In aluminium siloxides, reaction mixtures and reaction products to be employed according to the invention or according to the invention, both the radicals $R^{a'}$, $R^{a''}$, $R^{a'''}$ preferably have one of the meanings given above as preferred, and the groups X have a preferred meaning.

Thus, for example, in substituents —$SiR^{a'}R^{a''}R^{a'''}$, the radicals $R^{a'}$, $R^{a''}$, $R^{a'''}$ preferably independently of one another denote an optionally substituted radical which is chosen from the group consisting of:

$C_3$-$C_{25}$-aryl, $C_2$-$C_{25}$-heteroaryl, $C_4$-$C_{25}$-arylalkyl, $C_8$-$C_{25}$-cycloalkylaryl, $C_8$-$C_{25}$-cycloalkenylaryl, $C_5$-$C_{25}$-cycloalkylheteroaryl, $C_8$-$C_{25}$-heterocycloalkylaryl, $C_8$-$C_{25}$-heterocycloalkenylaryl, $C_8$-$C_{25}$-heterocycloalkenylheteroaryl and $C_3$-$C_{25}$-heteroarylalkyl, wherein X at the same time is chosen from the group consisting of $C_1$-$C_{20}$-alkyl (branched or unbranched), $C_3$-$C_8$-cycloalkyl; alkoxy having 1 to 30 C atoms; cycloalkoxy having a ring size of $C_3$-$C_{16}$; aryloxy having a ring size of $C_3$-$C_{30}$, diarylboronyl (wherein the aryl radicals are preferably phenyl or mesityl (2,4,6-trimethylphenyl); chloride.

Systems, e.g. aluminium siloxides, in which X has one of the meaning just mentioned, wherein at the same time $R^{a'}$, $R^{a''}$, $R^{a'''}$ independently of one another and independently of the meaning in a second substituent —$SiR^{a'}R^{a''}R^{a'''}$ optionally present are chosen from the group consisting of $C_6$-$C_{20}$-aryl, $C_3$-$C_{20}$-heteroaryl, $C_8$-$C_{20}$-cycloalkylaryl, $C_8$-$C_{20}$-cycloalkenylaryl, $C_7$-$C_{20}$-cycloalkylheteroaryl, $C_8$-$C_{20}$-heterocycloalkylaryl, $C_8$-$C_{20}$-heterocycloalkenylaryl and $C_8$-$C_{20}$-heterocycloalkenylheteroaryl, are particularly preferred.

Particularly preferred radicals $R^{a'}$, $R^{a''}$, $R^{a'''}$ from the group consisting of aryls are $C_6$-$C_{20}$-aryls, and in particular phenyl, 4-methoxyphenyl, 2,4-dimethoxyphenyl, 4-methylphenyl, 2,4-dimethylphenyl, 3,5-dimethylphenyl, 2-tert-butylphenyl, 4-tert-butylphenyl, 2,6-di-tert-butylphenyl, 4-$CF_3$-phenyl, 2,4-di-$CF_3$-phenyl, 1-naphthyl, 2-naphthyl, 9-anthracenyl and 9-phenanthrenyl.

Particularly preferred radicals $R^{a'}$, $R^{a''}$, $R^{a'''}$ from the group consisting of heteroaryls are $C_3$-$C_{20}$-heteroaryls, and in particular 2-furfuryl, 3-furfuryl and imidazolyl.

Particularly preferred radicals $R^{a'}$, $R^{a''}$, $R^{a'''}$ from the group consisting of cycloalkylaryls are $C_8$-$C_{20}$-cycloalkylaryls, and in particular indanyl and fluorenyl.

Particularly preferred radicals $R^{a'}$, $R^{a''}$, $R^{a'''}$ from the group consisting of cycloalkenylaryl are $C_8$-$C_{20}$-cycloalkenylaryl, and in particular indenyl.

Particularly preferred radicals $R^{a'}$, $R^{a''}$, $R^{a'''}$ from the group consisting of heterocycloalkenylaryl are $C_8$-$C_{20}$-heterocycloalkenylaryl, and in particular N—$C_1$-$C_{16}$-alkyl- and N—$C_1$-$C_8$-acyl-indolyl.

Particularly preferred radicals $R^{a'}$, $R^{a''}$, $R^{a'''}$ from the group consisting of heterocycloalkylaryl are $C_6$-$C_{20}$-heterocycloalkylaryl, and in particular N—$C_1$-$C_{16}$-alkyl- and N—$C_1$-$C_8$-acyl-indolinyl.

Particularly preferably, the preferred radicals $R^{a'}$, $R^{a''}$, $R^{a'''}$ are simultaneously present alongside particularly preferred radicals X.

Particularly preferred substituents X from the group consisting of alkyls are methyl, ethyl, n-propyl, iso-propyl, n-butyl, sec-butyl, iso-butyl, tert-butyl, alkyl having 5 to 30 C atoms. It is to be noted here that the compounds (including intermediates) disclosed in Can. J. Chem. 1992, 70, 771-778 are not the subject matter of the present invention.

Particularly preferably substituents X from the group consisting of alkoxy are $C_1$-$C_{20}$-alkoxy, such as methoxy, ethoxy, isopropoxy.

Particularly preferred substituents X from the group consisting of cycloalkoxy are $C_3$-$C_8$-cycloalkoxy, such as isopulegyl, menthyl.

Particularly preferred substituents X from the group consisting of aryloxy are $C_3$-$C_{15}$-aryloxy, such as phenoxy, 2-phenylphenoxy, 2,2'-diphenyldioxy, naphthoxy, 2,2'-binaphthyldioxy, 2,6-diphenylphenoxy.

Particularly preferred substituents X from the group consisting of boric acid substituted by one or two organic radicals are diarylboronyls, in particular bis(2,4,6-trimethylphenyl)boronate.

Examples of particularly preferred aluminium siloxides of the formulae (Ia) and (Ib) according to the invention which can be employed as catalysts in processes according to the invention are:

| Compound of the formulae (Ia) and (Ib): | $R^{a'}$ | $R^{a''}$ | $R^{a'''}$ | X |
|---|---|---|---|---|
| 1 | Ph | Ph | Ph | Me |
| 2 | 4-Me-Ph | 2,6-di-tert-butyl-Ph | Ph | Et |
|   | 4-Me-Ph | 2,6-di-tert-butyl-Ph | Ph | OMe |
| 3 | 4-CF$_3$-Ph | 2-naphthyl | 4-CF$_3$-Ph | 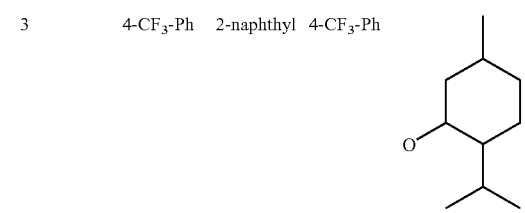 |
| 4 | 1-naphthyl | 1-naphthyl | 1-naphthyl | 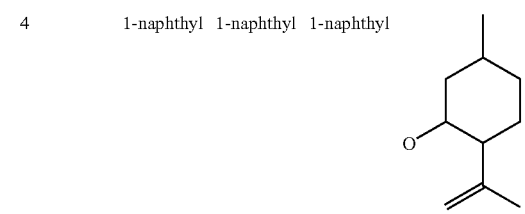 |
| 5 | 9-anthracenyl | Ph | Ph | 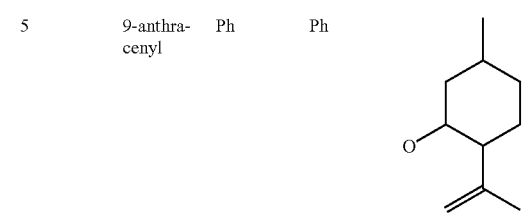 |
| 6 | 4-MeO-Ph | Ph | 4-MeO-Ph | hexyl |
| 7 | 2-furfuryl | Ph | Ph | 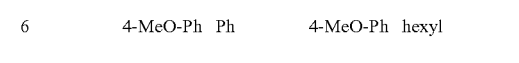 |
| 8 | indenyl | Ph | indenyl | OEt |
| 9 | fluorenyl | fluorenyl | fluorenyl | 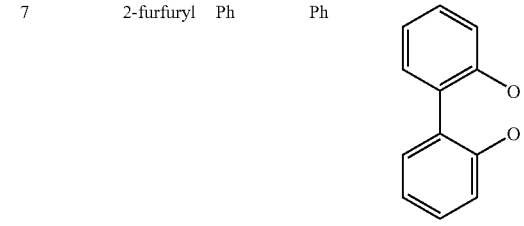 |
| 10 | 2-naphthyl | 2-naphthyl | 2-naphthyl | 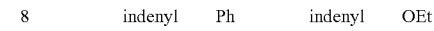 |
| 11 | 2-naphthyl | 2-naphthyl | 2-naphthyl | OEt |
| 12 | 2-naphthyl | 2-naphthyl | 2-naphthyl | Cl |

Abbreviations used: tert=tertiary, Ph=phenyl, Me=methyl, Et=ethyl

If the compound is a compound of the formula (Ib), the radicals $R^{a'}$, $R^{a''}$, $R^{a'''}$ in the two siloxy groups present are identical in the particularly preferred catalysts.

The preparation of the aluminium siloxides (Lewis acids) of the formulae (Ia) or (Ib) according to the invention is easiest if the particular radicals bonded to the same Si atom in the said formulae (Ia) and (Ib) are identical. Aluminium siloxides in which all the radicals $R^{a'}$, $R^{a''}$, $R^{a'''}$ in the siloxy group or the two siloxy groups have the same meaning are particularly easy to prepare.

The catalysts (aluminium siloxide compounds, mixtures and reaction products) to be employed according to the invention are particularly stable, which is advantageous for the use of the catalysts under industrial conditions, in particular since in contrast to the known systems the catalysts have a higher heat stability. The processes according to the invention can be carried out in a wide temperature range without loss in the selectivity, and lead reliably to the intramolecular reaction products sought.

The catalysts to be employed according to the invention (and in particular the novel aluminium siloxide compounds (Ia) and (Ib) according to the invention) are advantageously distinguished in that at comparatively high concentrations of compounds of the formula A, compared with the known Al-based catalysts, there is only a very slight tendency towards the formation of Tischtschenko-Claisen products. In addition to the high chemoselectivity, the diastereoselectivity is also particularly and surprisingly high when the catalysts to be used according to the invention are employed.

Preferably, for the preparation of an aluminium siloxide of the formulae (Ia) or (Ib) according to the invention, an aluminium compound of the formulae (IIIa) or (IIIb) which is chosen from the group consisting of trimethylaluminium, triethylaluminium, tripropylaluminium, tributylaluminium, triphenylaluminium, dimethylaluminium hydride, diethylaluminium hydride, dipropylaluminium hydride, dibutylaluminium hydride, methylaluminium dihydride, ethylaluminium dihydride, propylaluminium dihydride and butylaluminium dihydride is used as the starting substance, and trimethylaluminium and triethylaluminium are preferred.

The preparation of the aluminium siloxides of the formulae (Ia) or (Ib) according to the invention is preferably carried out by addition of a solution or dispersion of silanols of the formula (II) to the aluminium compound of the formulae (IIIa) or (IIIb) (e.g. present in solution), wherein the radicals $R^5$, X, $R^{a'}$, $R^{a''}$, $R^{a'''}$ in each case have the above-mentioned (preferred) meaning. The silanols (II) can be substituted by identical or different substituents; if the substituents in the silanols used are identical, the siloxy groups in the aluminium siloxide of the formula (Ib) are also identical. Preferably, the molar ratio of the total amount of aluminium compounds of the formulae (IIIa) or (IIIb) to the total amount of the one or the two different silanols of the formula (II) is greater than 1:3, preferably greater than 1.5:3 and particularly preferably greater than 2:3. So that as far as possible no aluminium compounds which carry three siloxy groups are formed in addition to the compounds of the formula (IIIa) and (IIIb) at this molar ratio, the process variant described above in which the aluminium compound is initially introduced into the reaction vessel is particularly advantageous.

The preparation of the aluminium siloxides of the formulae (Ia) or (Ib) or of the reaction product of the reaction of the aluminium compound of the formulae (IIIa) or (IIIb) with the silanol(s) (II) is conventionally carried out in diluents (preferably solvents) which are inert for the reactants, such as e.g. aromatic hydrocarbons, such as benzene, toluene or xylene (in this case preferably toluene), aliphatic hydrocarbons (such as heptane) or ethers (such as diethyl ether, diisopropyl ether or tetrahydrofuran). The aluminium siloxides of the formulae (Ia) or (Ib) or the said reaction products of the reaction of the aluminium compounds (IIIa) or (IIIb) with the silanol(s) (II) can also be prepared in high-boiling diluents, such as diphenyl ether or ditolyl ether. It is furthermore possible to prepare aluminium siloxides of the formulae (Ia) or (Ib) or the said reaction products in the same diluent in which the intramolecular Prins reaction is then carried out in a subsequent step (see below, in particular the examples).

In the processes according to the invention according to the second alternative, in which an aluminium compounds (IIIa) or (IIIb) is reacted with one or at least two different silanols of the formula (II) in step (b), the content of the silanol or of the silanols of the formula (II) in the reaction mixture is not decisive for the reaction with the aluminium compound of the formulae (IIIa) or (IIIb). The total content of silanols of the formula (II) is preferably between 30 and 1 wt. %, preferably between 20 and 5 wt. %, based on the total weight of the reaction mixture. The best results in the (in situ) preparation of catalysts (presumably of the formulae (Ia) or (Ib)) were obtained with total contents of compounds of the formula (II) of between 7.5 and 12.5 wt. %, based on the total weight of the reaction mixture.

The time required for the formation of an aluminium siloxide of the formula (Ia) or (Ib) is usually in the range of from 5 to 60 minutes.

Silanols of the formula (II) can be prepared, for example, by the following reaction route:

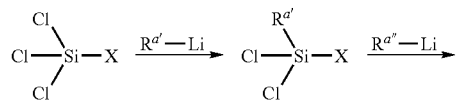

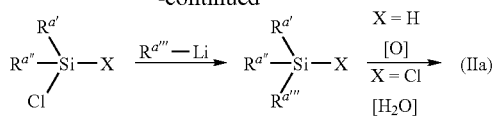

X = H, Cl

Depending on the desired substitution pattern, for the preparation of (II), for example starting from the chlorosilanes $HSiCl_3$ (see the above reaction route, X=H), $H_2SiCl_2$ or $H_3SiCl$, the chlorine atoms of the chlorosilane are exchanged successively or, if the radicals $R^a$ to $R^{c'''}$ are identical, also in one reaction step for the organic radical, preferably in the form of the corresponding lithium organyl (see the above reaction route and the examples below). A conversion of the silane formed in this way into the silanol of the formula (II) is then carried out by means of oxidation, for example with $KMnO_4$, in accordance with the process described in J. Organomet. Chem. 1995, 521, 229. The oxidation of the silanes can furthermore be carried out by other oxidation reagents, which likewise lead to the desired silanol of the formula (II) in high yields, such as e.g. ozone (Russ. Chem. Rev. 46 (10) 1977), homogeneous or heterogeneous ruthenium catalysts and water (J. Chem. Research 1997, 400) or also by free-radical reaction with N-hydroxyphthalimide (Synlett 2002, 7, 1173).

Starting from $SiCl_4$ (see the above reaction route, X=Cl), chlorosilanes of the type $(R^{a'})(R^{a''})(R^{a'''})SiCl$ can be prepared by sequential substitution, and can be converted into silanols of the formula (II) by subsequent hydrolysis of the Si—Cl bond. For example, commercially obtainable tert-butyl-chloro-diphenylsilane can be converted by means of hydrolysis into tert-butyldiphenylsilanol, for which in formula (II): $R^{a'}=R^{a''}=$phenyl, $R^{a'''}=$tert-butyl.

Preferably, lithium organyls or magnesium organyls, preferably lithium organyls, which contain the radicals $R^{a'}$, $R^{a''}$, $R^{a'''}$ are reacted with chlorosilanes in order to link the said radicals with the central Si atom. For the preparation of the lithium organyls, depending on the structure and CH acidity of the organyl, for example the corresponding bromine or iodine organyls can be used as starting substances (metal-halogen exchange) or, if the CH acidity is adequate, a direct lithiumation can be carried out. In both cases, the organyl is reacted with metallic lithium or a lithium-alkyl (such as, for example, methyllithium or butyllithium).

Some silanols of the formula (II) are commercially obtainable, such as, for example, triphenylsilanol, triethylsilanol or tert-butyldimethylsilanol. Furthermore, certain silanols of the formula (II) can be prepared from commercially obtainable compounds, such as chloromethyldiphenylsilane $MeSi(Ph)_2Cl$, by means of hydrolysis, or from dichlorodiphenylsilane $Ph_2SiCl_2$, for example by reaction with $R^{a''}$—Li analogously to the above equation to give $Ph_2Si(R^{a''})Cl$, from which an unsymmetric silanol of the formula (II) is obtained after hydrolysis, compare Example 2 below.

The aluminium siloxide of the formulae (Ia) or (Ib) or the said reaction product of the reaction of the aluminium compounds (IIIa) or (IIIb) with the silanol(s) (II) can be employed in substance or in a mixture with a diluent; the latter variant is advantageous in particular if the catalyst is to be freshly prepared and/or prepared in situ (in this context, see above).

The intramolecular Prins reaction can be carried out in the presence of one or more diluents or also without a diluent. In the diluent-free reaction procedure, a stirrability or homogenization of the reaction mixture is ensured by educt A and/or reaction product B.

Suitable diluents for carrying out the intramolecular Prins reaction are, for example, aromatic hydrocarbons, such as benzene, toluene, xylene, diphenyl, diphenylethane (dibenzyl), dodecylbenzene or dibenzylbenzenes, saturated hydrocarbons, such as hexane, heptane, octane, cyclohexane or methylcyclohexane, ethers, such as diethyl ether, diisopropyl ether, tetrahydrofuran, dioxane, dioxolane, dimethoxyethane, diphenyl ether (diphenyl oxide) or ditolyl ether, and mixtures of these diluents.

The intramolecular Prins reaction is preferably carried out according to the invention in one or more high-boiling diluents (having a boiling point above 220° C., preferably above 240° C., in each case under 1013 mbar), such as diphenyl, diphenyl ether or ditolyl ether or mixtures thereof (such as, for example, "diphyl", a eutectic mixture of 26.5% diphenyl and 73.5% diphenyl oxide, e.g. commercially obtainable under the name Dowtherm® A), since with these diluents, after the reaction has ended it is possible to distil off the lower-boiling reaction products of the formula B (and, where appropriate, unreacted amounts of the educts of the formula A), whereby the catalyst remaining in the distillation bottom products (e.g. the aluminium siloxide of the formula (I)) is not or not noticeably destroyed and in this manner the catalyst solution already employed can be employed for further reaction cycles.

Overall, with the catalysts to be employed according to the invention or according to the invention, a continuous reaction procedure is possible, also on the basis of the comparatively short reaction times of the intramolecular Prins reaction which can be achieved herewith. If a high-boiling diluent is employed in carrying out the intramolecular Prins reaction, the process can be operated overall continuously, for example, by means of adequately known devices, such as a stirred tank or a cascade of stirred tanks and a rectification column. In this context, the reaction mixture is introduced continuously between the rectifying and stripping part of the rectification column, the catalyst together with the high-boiling diluent being obtained in the stripping part and being recycled back to the stirred tank or the cascade of stirred tanks, and it being possible for the desired product of the formula B to be removed in the rectifying part.

If the intramolecular Prins reaction is carried out without a diluent, the addition of a high-boiling diluent (as defined above) before carrying out the distillation is advantageous. In this manner, all the lower-boiling reaction products of the formula B (and, where appropriate, unreacted amounts of the educts of the formula A) can be distilled off, at the same time the stirrability of the distillation bottom product being ensured and the crystallization, precipitation or caking and an (uncontrolled) overheating of the catalyst remaining in the bottom product (in particular an aluminium siloxide of the formula (I)) being avoided.

The catalysts of the formula (I) have a high heat stability. The intramolecular Prins reaction is preferably carried out according to the invention at a temperature in the range of from −10 to 130° C., preferably in the range of from 0 to 60° C., and particularly preferably in the range of 10 to 50° C.

According to the invention, the intramolecular reaction proceeds very rapidly compared with the known catalyst systems, and is regularly concluded within a reaction time of 1-4 hours under the stated reaction conditions (conversion >98%).

The following examples illustrate the invention. Unless stated otherwise, all the data relate to the weight.

EXAMPLE 1

Preparation of Trisarylsilanols of the Formula (II)

1.1 General Instructions for the Preparation of Trisarylsilanols of the Formula (II)

The silanols are prepared in accordance with the methods described in the literature for building up arylsilanes and -silanols.

For this, the aryl bromide in question is reacted with the equimolar amount of n-butyllithium in diethyl ether at −20 to −40° C. under an inert gas atmosphere (usually nitrogen or argon). After 5 h and warming to room temperature, approx. 0.33 molar equivalent of a 5 wt. % strength solution of silicon-chloroform (trichlorosilane) $HSiCl_3$ in diethyl ether is added to the reaction mixture. The reaction mixture is then heated under reflux for 3 h.

After cooling, 5 molar equivalents of water are added to the reaction mixture, and the trisarylsilane formed is obtained as a solid.

The trisarylsilane formed in this way is oxidized as an about 10 wt. % strength solution in tetrahydrofuran (THF) with potassium permanganate (regularly 1.5 to 5 molar equivalents) to give the silanol of the formula (II). The silanol of the formula (II) obtained is then separated off by filtration from the pyrolusite (manganese dioxide) formed. The colourless solution obtained is finally concentrated in vacuo.

The silanol of the formula (II) is generally obtained in the form of a white to yellowish solid.

1.2 Preparation of tris(1-naphthyl)silanol

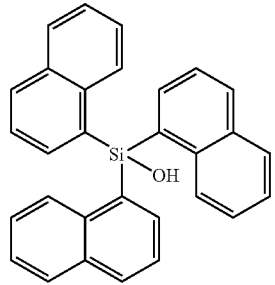

Analogously to Example 1.1, 100 mmol 1-naphthyl bromide were reacted with 100 mmol n-butyllithium (2M solution in cyclohexane). The naphthyllithium formed was then reacted with 33 mmol silicon-chloroform (trichlorosilane) analogously to Example 1.1.

Tris(1-naphthyl)silane was obtained as a white solid in a purity of 99% (GC-MS), yield: 13 g.

As described in Example 1.1, the reaction to give tris(1-naphthyl)silanol was carried out by the oxidation reaction with potassium permanganate.

For this, 9.5 mmol of the tris(1-naphthyl)silane are initially introduced into 100 ml THF. 15 mmol of solid potassium permanganate are then added to the solution and the solution is stirred at room temperature (about 20° C.) for 2 days.

The pyrolusite ($MnO_2$) which forms is separated off by filtration over silica gel. The organic solution of the tris(1-naphthyl)silanol is finally concentrated and the silanol is obtained in the form of a white solid. Yield: 4.04 g (corresponds to 95% of theory).

1.3 Preparation of tris(9-anthracenyl)silanol

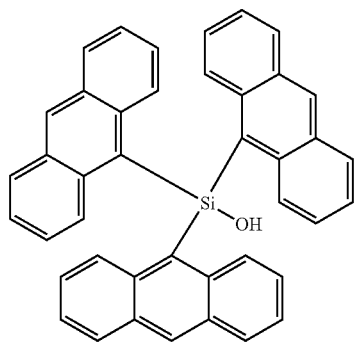

Analogously to Example 1.1, for the preparation of tris(9-anthracenyl)silane, 60 mmol 9-anthracenyl bromide were reacted with the equimolar amount of n-butyllithium (2 M solution, 60 mmol) in diethyl ether at −40° C. and the solution was then warmed to room temperature (about 20° C.). After cooling the reaction solution to −20° C., this is reacted with 20 mmol silicon-chloroform (trichlorosilane) and the resulting white suspension is then warmed to room temperature. Thereafter, the reaction mixture is heated under reflux for 3 h. After adding 100 g water to the reaction mixture, tris(9-anthracenyl)silane is filtered off as a yellow solid. Crude yield: 12.3 g, purity: 85.4% (GC-MS). The silane is purified by crystallization from ethanol.

The oxidation of the tris(9-anthracenyl)silane is carried out analogously to Example 1.1 with 5 molar equivalents of potassium permanganate in boiling tetrahydrofuran. The reaction is interrupted after 15 h and, after filtration over silica gel to separate off pyrolusite from the solution, the silanol formed is obtained as a yellowish solid by concentration of the reaction mixture, yield: 10.75 g with a purity of 85% (GC-MS). Further purification is carried out by crystallization from boiling ethanol.

EXAMPLE 2

Preparation of Unsymmetrically Substituted Triarylsilanols 2.1 General Instructions for the Preparation of Unsymmetrically Substituted Triarylsilanols of the Formula (II), in Particular of Diphenylarylsilanols For the preparation of unsymmetric triarylsilanols, the lithiumated aryl halide (preferably lithiumated aryl bromide) is reacted with diaryldichlorosilane, e.g. dichlorodiphenylsilane $Ph_2SiCl_2$.

The aryl bromide employed by way of example is metallized analogously to Example 1.1 with the equimolar amount of n-butyllithium at 40 to −20° C. in diethyl ether and, after warming to room temperature (approx. 20° C.) is reacted for 5 h with an equimolar amount of the dichlorodiphenylsilane employed by way of example, dissolved in diethyl ether. After warming the reaction solution to room temperature, the reaction mixture is heated under reflux for 3 h. Thereafter, for preparation of the silanol water is added to the white suspension formed and the reaction mixture is heated again under reflux for 1 h. The organic phase obtained after separating off the aqueous phase is washed neutral with 5 wt. % strength sodium carbonate solution and concentrated in vacuo. The unsymmetrically substituted triarylsilanols are obtained as white to yellowish solids.

2.2 Preparation of (9-anthracenyl)diphenylsilanol

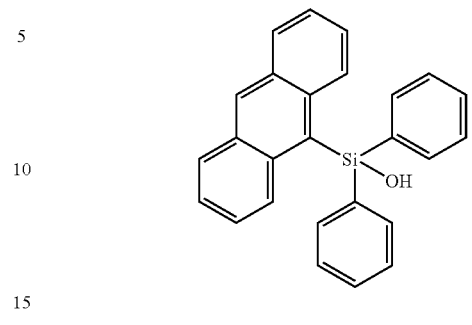

For preparation of the silanol, 20 mmol 9-anthracenyl bromide are metallized with the equimolar amount of n-butyllithium (2 M solution in cyclohexane, 20 mmol) at −20° C. and dichlorodiphenylsilane is then added, in accordance with Example 2.1. When the addition of the dichlorodiphenylsilane has ended, the reaction mixture is heated under reflux for 3 h and then hydrolysed by addition of water (100 g).

After the organic phase which has been separated off has been washed neutral, the solution is concentrated in vacuo and the crude product is obtained as a yellow solid. Crude yield: 5.80 g, content: 69% (GC-MS).

2.3 Preparation of (1-naphthyl)diphenylsilanol

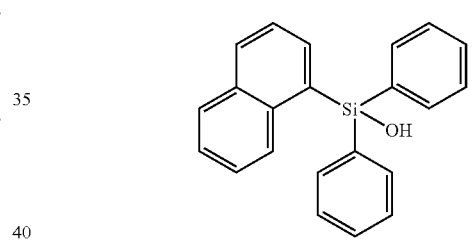

For preparation of the silanol, 60 mmol 1-naphthyl bromide are metallized with the equimolar amount of n-butyllithium (2 M solution in cyclohexane, 60 mmol) at −20° C. in 400 ml diethyl ether and 60 mmol dichlorodiphenylsilane is then added, in accordance with Example 2.1. After addition of the dichlorodiphenylsilane, the reaction mixture is heated under reflux for 3 h and then hydrolysed by addition of water (100 g). After the organic phase which has been separated off has been washed neutral, the solution is concentrated in vacuo and the crude product is obtained as a white solid. Crude yield: 21.17 g, content: 84% (GC-MS).

EXAMPLES 3 AND 4

Preparation of Isopulegol

General Instructions for Carrying Out the Cyclization (Intramolecular Prins Reaction)

The experiments for preparation of isopulegol from citronella were carried out using anhydrous diluents and under an inert gas atmosphere (nitrogen or argon).

EXAMPLES 3.1-3.2

Comparison Example: Preparation of Isopulegol (Analogously to EP 1 225 163 A2 not According to the Invention)

3.1: Preparation of tris(2,6-diphenylphenoxy)aluminium (Catalyst not According to the Invention)

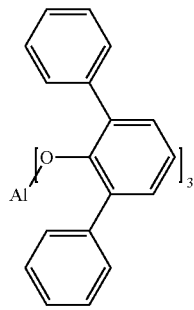

3 mmol 2,6-diphenylphenol are initially introduced into toluene under an inert gas. After the 2,6-diphenylphenol has dissolved, 1 mmol triethylaluminium (solution in toluene) is added dropwise to the cooled solution at about 0° C. and the reaction mixture is stirred at room temperature for 1 h. During this procedure, the solution assumes a pale yellowish colour shade, but remains clear.

3.2: Cyclization

The reaction solution from 3.1 is diluted with 50 ml toluene and cooled to −10° C. 50 mmol of racemic citronellal are added dropwise to the cold reaction solution over a period of 5 minutes.

Monitoring of the reaction (GC) showed a conversion of 63% after 4 h. Complete conversion was achieved after 20 h, and the selectivity, based on isopulegol and its stereoisomers B2, was 75%, yield: 7.70 g (50 mmol).

EXAMPLE 3.3

Comparison Example: Preparation of Isopulegol (Analogously to Synthesis 1978, 147, not According to the Invention)

0.001 mmol zinc bromide is initially introduced into 70 ml toluene under an inert gas. The reaction solution is then temperature-controlled at 85° C. and 0.05 mol citronellal are metered into the reaction solution. The heterogeneous reaction mixture is then stirred at this temperature for 4 h. Thereafter, the reaction mixture is washed with 50 ml 15% strength sodium hydroxide solution and, after washing neutral, the solvent is removed from the reaction mixture under reduced pressure.

A conversion of 98% was achieved, and the selectivity, based on isopulegol and its stereoisomers B2, was 85%, yield: 50 mmol in the form of a yellow oil.

EXAMPLES 4-12

Intramolecular Prins Reaction, According to the Invention, of Citronellal to Give Isopulegol

EXAMPLE 4

1.8 mmol tri(1-naphthyl)silanol in toluene are slowly added dropwise to a solution of 1 mmol triethylaluminium in toluene at room temperature. Thereafter, the reaction mixture is further stirred at room temperature (approx. 20° C.), the suspension first becoming significantly lighter in colour and then clear. To bring the formation of aluminium siloxides of the formulae (Ia) and (Ib) to completion, the reaction mixture is stirred at room temperature for a further 30 min.

100 mmol citronellal as a 50% strength solution in toluene were then added dropwise into the solution containing 1 mmol of the freshly prepared aluminium siloxides. When the metering in had ended, the reaction mixture was stirred at room temperature for a further 4 h and the reaction was then interrupted by addition of 50 ml 15% strength sodium hydroxide solution. After washing neutral and distilling off the solvent, the reaction product B2 was obtained as a colourless oil, yield: 15.5 g, 100 mmol.

A conversion of 99% was achieved, and the selectivity, based on isopulegol and its stereoisomers B2, was >99.5%. No Tischtschenko-Claisen products were found. The selectivity for B2 iso in the product was 95%.

EXAMPLE 5

The aluminium siloxide (Ia) or (Ib) was prepared analogously to Example 4. The solution containing 1 mmol of the freshly prepared aluminium siloxide catalyst was then heated to 60° C. and 100 mmol citronellal were added dropwise. When the metering in had ended, the reaction mixture was stirred at 60° C. for a further 2 h and the reaction was then interrupted by addition of 50 ml 15% strength sodium hydroxide solution. After washing neutral and distilling off the solvent, the reaction product B2 was obtained as a colourless oil, yield: 15.4 g.

A conversion of 98% was achieved, and the selectivity, based on isopulegol and its stereoisomers B2, was 98%. No Tischtschenko-Claisen products were found. The diastereoselectivity for B2 iso was 93%.

EXAMPLE 6

The aluminium siloxide (Ia) or (Ib) was prepared by reaction of 1.8 mmol triphenylsilanol and 1 mmol triethylaluminium. 100 mmol citronellal were then added dropwise at room temperature to the solution containing 1 mmol of the freshly prepared aluminium siloxide derivative (I) in the course of 30 min. When the metering in had ended, the reaction mixture was stirred at the same temperature for a further 2 h and the reaction was then interrupted by addition of 20% strength sodium hydroxide solution. After washing neutral and distilling off the solvent, the reaction product B2 was obtained as a colourless oil, yield: 30.0 g.

A conversion of 97% was achieved, and the selectivity, based on isopulegol and its stereoisomers B2, was >99.5%. No Tischtschenko-Claisen products were found.

EXAMPLE 7

1 mmol diethylaluminium chloride is initially introduced into 20 ml toluene. 1.8 mmol triphenylsilanol are added to this solution. The suspension formed becomes clear after a preforming time of 25 minutes at room temperature. Citronellal (100 mmol, 15.4 g) is then added dropwise to the clear solution over a period of 10 minutes and the mixture is stirred at room temperature for 2 hours. After destruction of the catalyst by addition of 15% strength NaOH, the organic phase is washed neutral and the diluent is distilled off. The cyclization product is obtained as a colourless oil (15.5 g, 100 mmol).

The crude product comprises exclusively the cyclization product B2. The diastereoselectivity for isopulegol B2 iso is 75%. No Tischtschenko-Claisen products were found.

EXAMPLE 8

1 mmol diethylaluminium chloride is initially introduced into 20 ml toluene. 1.8 mmol tri(1-naphthyl)silanol are added to this solution. The suspension formed becomes clear after a preforming time of 25 minutes at room temperature. Citronellal (100 mmol, 15.4 g) is then added dropwise to the clear solution over a period of 10 minutes and the mixture is stirred at room temperature for 2 hours. After destruction of the catalyst by addition of 15% strength sodium hydroxide solution, the organic phase is washed neutral and the diluent is distilled off. The cyclization product is obtained as a colourless oil (14.9 g).

The crude product comprises exclusively the cyclization product B2. The diastereoselectivity for isopulegol B2 iso is 95%. No Tischtschenko-Claisen products were found.

EXAMPLE 9

Procedure for Cyclization Reactions with Aluminium Siloxide Catalysts of Type (Ia) or (Ib) where X=OR The preparation of the catalyst is carried out as described in Example 4. After a preforming period of the catalyst (Ia) or (Ib), prepared from 1 mmol triethylaluminium and the corresponding amount of the silanol (>1 to ≦2 mmol), of 15 minutes at room temperature, the desired radical X is added in the form of its alcohol (ROH) to the reaction mixture at room temperature and the preforming is continued for 15 minutes. The amount of alcohol added is determined here by the amount of silanol previously added. Citronellal (100 mmol, 15.4 g) is then added dropwise to the reaction mixture. After 3 h the reaction is interrupted by addition of 15% strength sodium hydroxide solution and the organic phase is washed neutral.

The yields and compositions of various examples can be found in the table below.

| Run | Formula (II) $R^{a'}, R^{a'''}, R^{a''''}$ | Equiv. | X | Equiv. | Yield % B2 | Diastereosel. % B2iso |
|---|---|---|---|---|---|---|
| 1 | naphthyl | 1 | OEt | 2 | 91 | 96 |
| 2 | naphthyl | 1 | OiPr | 2 | 92 | 96 |
| 3 | naphthyl | 2 | isopulegol-O- (with isopropenyl) | 1 | 91 | 95 |
| 4 | naphthyl | 1 | isopulegol-O- (with isopropenyl) | 2 | 94 | 94 |
| 5 | naphthyl | 2 | menthol-O- (with isopropyl) | 1 | 99 | 93 |
| 6 | naphthyl | 1 | menthol-O- (with isopropyl) | 2 | 97 | 92 |
| 7 | phenyl |  | 2,6-diphenyl phenol |  | 99 | 80 |

-continued

| Run | Formula (II) R$^{a'}$, R$^{a''}$, R$^{a'''}$ | Equiv. | X | Equiv. | Yield % B2 | Diastereosel. % B2iso |
|---|---|---|---|---|---|---|
| 8 | phenyl | 2 | *menthol-type structure with isopropenyl group* | 1 | 99 | 75 |
| 9 | phenyl | 1 | *menthol-type structure with isopropenyl group* | 2 | 99 | 75 |
| 10 | phenyl | 2 | *menthol structure with isopropyl group* | 12 | 99 | 75 |
| 11 | naphthyl | 1 | *BINOL structure* | 1 | 95 | 89 |
| 12 | naphthyl | 1 | *biphenyl-2,2'-diol structure* | 1 | 90 | 89 |
| 13 | naphthyl | 2 | *tetramethyl dibenzaborole–O structure* | 1 | 99 | 92 |

-continued

| Run | Formula (II) $R^{a'}, R^{a'''}, R^{a''''}$ | Equiv. | X | Equiv. | Yield % B2 | Diastereosel. % B2iso |
|---|---|---|---|---|---|---|
| 14 | naphthyl | 2 | (2-phenylphenoxy) | 1 | 99 | 93 |
| 15 | naphthyl | 1 | (2-phenylphenoxy) | 2 | 99 | 81 |

EXAMPLE 10

The aluminium siloxide (Ia) or (Ib) was prepared analogously to Example 4 in 5 ml Marlotherm S® (isomer mixture of isomeric dibenzyltoluenes). 200 mmol citronellal were then added at room temperature to a solution containing 2 mmol of freshly prepared aluminium siloxide over a period of 15 min. When the metering in had ended, the reaction mixture was stirred at room temperature for a further 2 h and the reaction was then interrupted by addition of 50 ml 15% strength sodium hydroxide solution. After washing neutral and distilling off the solvent, the reaction product B2 was obtained as a colourless oil, yield: 14.8 g.

A conversion of 99% was achieved, and the selectivity, based on isopulegol and its stereoisomers B2, was 98%. No Tischtschenko-Claisen products were found. The diastereoselectivity for B2 iso was 93%.

EXAMPLE 11

The aluminium siloxide derivative (Ia) or (Ib) was prepared analogously to Example 4 in 5 ml Marlotherm S® (isomer mixture of dibenzyltoluenes). 200 mmol citronellal were then added at room temperature to a solution containing 2 mmol of freshly prepared aluminium siloxide over a period of 15 min. When the metering in had ended, the reaction mixture was stirred at room temperature for a further 2 h and the reaction product was then distilled off from the reaction mixture in vacuo at a maximum of 120° C. After cooling to room temperature, citronellal was added again to the catalyst solution recovered. The results of the two runs can be found in the following table.

| Run | $R^{a'}$-$R^{a'''}$ | Equiv. | X | Equiv. | Yield % B2 | Diastereosel. % B2iso |
|---|---|---|---|---|---|---|
| 1 | naphthyl | 2 | Et | 1 | 99 | 95 |
| 2 | naphthyl | 2 | Et | 1 | 99 | 93 |

No Tischtschenko-Claisen products were found.

EXAMPLE 12

Cyclization of Citronellal to Isopulegol 1.8 mmol tri(1-naphthyl)silanol in toluene are slowly added dropwise to a solution of 1 mmol triethylaluminium in toluene at room temperature. Thereafter, the reaction mixture is further stirred at room temperature (approx. 20° C.), the suspension first becoming significantly lighter in colour and then clear. To bring the formation of aluminium siloxides of the formulae (Ia) and (Ib) to completion, 1 mmol acetic acid, dissolved in toluene, is slowly added to the reaction mixture. The reaction mixture is then stirred at room temperature for a further 30 min.

100 mmol citronellal as a 50% strength solution in toluene were then added dropwise into the solution containing 1 mmol of the freshly prepared aluminium siloxides. When the metering in had ended, the reaction mixture was stirred at room temperature for a further 4 h and the reaction was then interrupted by addition of 50 ml 15% strength sodium hydroxide solution. After washing neutral and distilling off the solvent, the reaction product B2 was obtained as a colourless oil, yield: 15.5 g, 100 mmol.

A conversion of 99% was achieved, and the selectivity, based on isopulegol and its stereoisomers B2, was >99%. No Tischtschenko-Claisen products were found. The selectivity for B2 iso in the product was 93%.

EXAMPLE 13

Cyclization of Citronellal to Isopulegol 1.8 mmol tri(1-naphthyl)silanol in toluene are slowly added dropwise to a solution of 1 mmol triethylaluminium in toluene at room temperature. Thereafter, the reaction mixture is further stirred at room temperature (approx. 20° C.), the suspension first becoming significantly lighter in colour and then clear. To bring the formation of aluminium siloxides of the formulae (Ia) and (Ib) to completion, 1 mmol propionic acid, dissolved in toluene, is slowly added to the reaction mixture. The reaction mixture is then stirred at room temperature for a further 30 min.

100 mmol citronellal as a 50% strength solution in toluene were then added dropwise into the solution containing 1 mmol of the freshly prepared aluminium siloxides. When the metering in had ended, the reaction mixture was stirred at room temperature for a further 4 h and the reaction was then interrupted by addition of 50 ml 15% strength sodium hydroxide solution. After washing neutral and distilling off the solvent, the reaction product B2 was obtained as a colourless oil, yield: 15.5 g, 100 mmol.

A conversion of 99% was achieved, and the selectivity, based on isopulegol and its stereoisomers B2, was >99%. No Tischtschenko-Claisen products were found. The selectivity for B2 iso in the product was 92%.

The invention claimed is:

1. A process for the preparation of a compound of the formula B

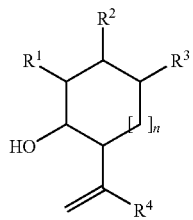

comprising:
providing a compound of the formula A

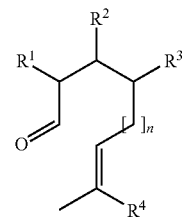

reacting the compound of the formula A in an intramolecular reaction in the presence of an aluminium siloxide of the formula (Ia) or (Ib)

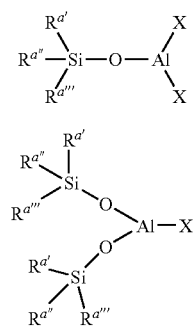

wherein $R^1, R^2, R^3$ in each case independently of one another are hydrogen or methyl,
$R^4$ is hydrogen or an alkyl radical having 1 to 6 C atoms,
n is 0, 1 or 2; and $R^{a'}, R^{a''}, R^{a'''}$ in each case independently of one another and, for formula (Ib), independently of the meaning in a second substituent $-SiR^{a'}R^{a''}R^{a'''}$ are hydrogen or an organic radical, with the proviso that at least one of the radicals $R^{a'}, R^{a''}, R^{a'''}$ of each substituent $-SiR^{a'}R^{a''}R^{a'''}$ is not hydrogen; and
independently of one another two or three of the radicals $R^{a'}, R^{a''}, R^{a'''}$ of each substituent $-SiR^{a'}R^{a''}R^{a'''}$ may be covalently bonded to one another; and
X in each case independently is an organic or inorganic substituent, but not hydrogen or a siloxy group having a substituent $-SiR^{a'}R^{a''}R^{a'''}$ as defined above.

2. The process of claim 1, wherein in each case X independently is an organic or inorganic substituent which is chosen from the group consisting of branched or unbranched or cyclic alkyl, alkenyl or alkynyl having 1 to 30 C atoms; alkoxy having 1 to 30 C atoms; cycloalkoxy having a ring size of $C_3$-$C_{16}$; aryloxy; bisaryloxy; boric acid substituted by one or two organic radicals; and chloride.

3. The process of claim 1, wherein each X independently is methyl, ethyl, n-propyl, iso-propyl, n-butyl, sec-butyl, iso-butyl, tert-butyl, alkoxy having 1 to 10 C atoms, cycloalkoxy having a ring size of $C_3$-$C_8$ or chloride.

4. The process of claim 1, wherein
$R^1$ and $R^2$ in each case independently of one another are hydrogen or methyl,
$R^3$ is hydrogen,
$R^4$ is methyl, and
n is 0 or 1.

5. The process of claim 1, wherein the compound of the formula A is selected from the group consisting of 2,6-dimethyl-5-heptenal and citronellal (3,7-dimethyl-6-octenal).

6. The process of claim 1, wherein the intramolecular reaction of the compound of the formula A is carried out in a diluent, the boiling point of which is higher than that of the compounds of the formulae A and B; or
after the intramolecular reaction of the compound of the formula A has taken place, a diluent, the boiling point of which is higher than that of the compounds of the formulae A and B, is added,
said process further comprising:
separating off, by distillation, the compound of the formula B from the diluent and the aluminium siloxide of the formula (Ia) or (Ib).

7. The process according to claim 1, further comprising:
recycling the aluminium siloxide of the formula (Ia) or (Ib) in the intramolecular reaction of the compound of the formula A.

8. The process of claim 1, wherein $R^{a'}, R^{a''}, R^{a'''}$ in each case independently are a substituted or unsubstituted radical which is chosen from the group consisting of $C_1$-$C_{20}$-alkyl, $C_1$-$C_{20}$-heteroalkyl, $C_3$-$C_{20}$-cycloalkyl, $C_4$-$C_{20}$-cycloalkylalkyl, $C_2$-$C_{20}$-alkenyl, $C_3$-$C_{20}$-cycloalkenyl, $C_4$-$C_{20}$-cycloalkenylalkyl, $C_2$-$C_{20}$-alkynyl, $C_5$-$C_{20}$-cycloalkylalkynyl, $C_1$-$C_{20}$-alkoxy, $C_3$-$C_{20}$-cycloalkoxy, $C_5$-$C_{20}$-cycloalkylalkoxy, $C_3$-$C_{25}$-aryl, $C_2$-$C_{25}$-heteroaryl, $C_4$-$C_{25}$-arylalkyl, $C_8$-$C_{25}$-cycloalkylaryl, $C_8$-$C_{25}$-cycloalkenylaryl, $C_5$-$C_{25}$-cycloalkylheteroaryl, $C_8$-$C_{25}$-heterocycloalkylaryl, $C_8$-$C_{25}$-heterocycloalkenylaryl, and $C_8$-$C_{25}$-heterocycloalkenylheteroaryl and $C_3$-$C_{25}$-heteroarylalkyl,
wherein independently of one another also two or three of the radicals $R^{a'}, R^{a''}, R^{a'''}$ can be covalently bonded to one another.

9. The process of claim 1, wherein $R^{a'}, R^{a''}, R^{a'''}$ in each case independently are an optionally substituted radical chosen from the group consisting of $C_3$-$C_{25}$-aryl, $C_2$-$C_{25}$-heteroaryl, $C_4$-$C_{25}$-arylalkyl, $C_8$-$C_{25}$-cycloalkylaryl, $C_8$-$C_{25}$- cycloalkenylaryl, C$_5$-C$_{25}$-cycloalkylheteroaryl, C$_8$-C$_{25}$-heterocycloalkylaryl, C$_8$-C$_{25}$-heterocycloalkenylaryl, C$_8$-C$_{25}$-heterocycloalkenylheteroaryl and C$_3$-C$_{25}$-heteroarylalkyl.

10. The process of claim 1, wherein

R$^{a'}$, R$^{a''}$, R$^{a'''}$ in each case independently are a substituted or unsubstituted radical chosen from the group consisting of C$_6$-C$_{20}$-aryl, C$_3$-C$_{20}$-heteroaryl, C$_8$-C$_{20}$-cycloalkylaryl, C$_8$-C$_{20}$-cycloalkenylaryl, C$_7$-C$_{20}$-cycloalkylheteroaryl, C$_8$-C$_{20}$-heterocycloalkylaryl, C$_8$-C$_{20}$-heterocycloalkenylaryl and C$_8$-C$_{20}$-heterocycloalkenylheteroaryl.

11. The process of claim 1, wherein all the radicals R$^{a'}$, R$^{a''}$, R$^{a'''}$ are identical.

12. A process for the preparation of a compound of the formula B

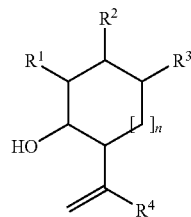

B comprising:

(a) providing a compound of the formula A

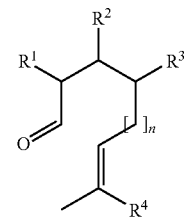

A (b) reacting an aluminium compound of the formula (IIIa) or (IIIb)

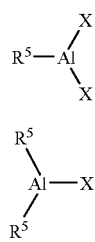

(IIIa)

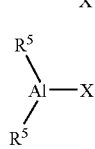

(IIIb)

wherein each R$^5$ is the same or different and is an alkyl radical having 1 to 4 C atoms or an aryl radical or hydrogen; and X is an alkyl radical having 1 to 4 C atoms or chloride, with the proviso that X is bonded to Al more firmly than or as firmly as R$^5$;

with one or more different silanols of the formula (II),

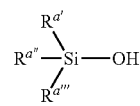

(II)

wherein:

R$^{a'}$, R$^{a''}$, R$^{a'''}$ in each case independently are hydrogen or an organic radical, with the proviso that at least one of the radicals R$^{a'}$, R$^{a''}$, R$^{a'''}$ in each silanol employed is not hydrogen;

independently of one another also two or three of the radicals R$^{a'}$, R$^{a''}$, R$^{a'''}$ in each of the silanols employed can be covalently bonded to one another; and the molar ratio of aluminium compound of the formula (IIIa) or (IIIb) to the total amount of the one or more different silanols of the formula (II) is greater than 1:3; and (c) in situ and/or within 1 hour after the start of the reaction according to step (b), contacting of the compound of the formula A with the reaction product obtained in step (b) under conditions such that an intramolecular reaction of the compound of the formula A occurs to produce a compound of the formula B;

wherein R$^1$, R$^2$, R$^3$ in each case independently of one another are hydrogen or methyl, R$^4$ is hydrogen or an alkyl radical having 1 to 6 C atoms, and n is 0, 1 or 2.

13. The process of claim 12, wherein

R$^1$ and R$^2$ in each case independently of one another are hydrogen or methyl, R$^3$ is hydrogen, R$^4$ is methyl, and n is 0 or 1.

14. A process comprising undergoing a chemical reaction in the presence of a catalyst selected from the group consisting of:

an aluminium siloxide of the formula (Ia) or (Ib)

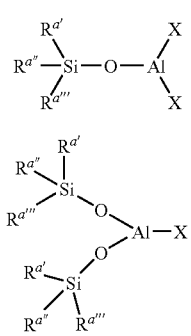

(Ia)

(Ib)

wherein X in each case independently is an organic or inorganic substituent;

a reaction product of a reaction of an aluminium compound of the formula (IIIa) or (IIIb)

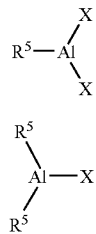 (IIIa)

(IIIb)

wherein
R⁵ is an alkyl radical having 1 to 4 C atoms, an aryl radical or hydrogen, and
X is an alkyl radical having 1 to 4 C atoms or chloride, with the proviso that X is bonded to Al more firmly than or as firmly as R⁵;
with one or more different silanols of the formula (II),

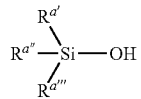 (II)

wherein the molar ratio of aluminium compound of the formula (IIIa) or (IIIb) to the total amount of the one or the various silanols of the formula (II) is greater than 1:3, and further wherein in formula Ia, Ib, and II
$R^{a'}, R^{a''}, R^{a'''}$ in each case independently are hydrogen or an organic radical, with the proviso that at least one of the radicals $R^{a'}, R^{a''}, R^{a'''}$ in each silanol or siloxide employed is not hydrogen, and
independently of one another also two or three of the radicals $R^{a'}, R^{a''}, R^{a'''}$ in each of the substituents —$SiR^{a'}R^{a''}R^{a'''}$ or each of the silanols employed may be covalently bonded to one another.

15. The process of claim 14, wherein the chemical reaction is an intramolecular Prins reaction.

16. The process of claim 14, wherein the chemical reaction produces a compound of the formula B

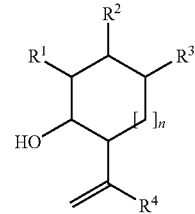 B from a compound of the formula A

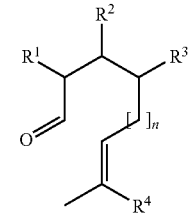 A wherein in the formulae A and B, $R^1, R^2, R^3, R^4$ and n in each case have the same meaning and
$R^1, R^2, R^3$ in each case independently of one another are hydrogen or methyl,
$R^4$ is hydrogen or an alkyl radical having 1 to 6 C atoms, and
n is 0, 1 or 2.

* * * * *